United States Patent [19]
Glover et al.

[11] Patent Number: 5,505,854
[45] Date of Patent: Apr. 9, 1996

[54] TWO CONTINUOUS FILTRATION SYSTEM FOR SUPPLYING FILTRATE TO AUTOMATIC ANALYZERS

[75] Inventors: Robert L. Glover, Southlake, Tex.;
Robert E. Moser, Palo Alto, Calif.;
Frank Meserole, Austin; Carl
Richardson, Round Rock, both of Tex.;
Gerard B. Maybach, Getzville, N.Y.;
Gordon Maller, Louisville, Ky.;
Timothy Hanley, Holly Springs, N.C.;
Thomas King, Wyomissing, Pa.

[73] Assignee: Electric Power Research Institute, Palo Alto, Calif.

[21] Appl. No.: 302,432

[22] Filed: Sep. 9, 1994

[51] Int. Cl.⁶ .......................... B01D 65/02; B01D 17/12
[52] U.S. Cl. .................... 210/739; 210/96.2; 210/143;
210/321.69; 210/333.01; 210/636; 210/798;
422/62; 423/243.08; 436/177
[58] Field of Search ..................... 210/96.1, 108,
210/333.01, 335, 321.69, 411, 427, 636,
739, 798, 902, 500.35, 96.2, 143, 650;
95/8, 13; 423/243.08, 243.09; 55/270; 422/62;
436/177

[56] References Cited

U.S. PATENT DOCUMENTS

| 3,421,835 | 1/1969 | McCarty | 210/333.1 |
| 3,598,238 | 8/1971 | Collins, Jr. | 210/138 |
| 4,178,248 | 12/1979 | Porter et al. | 210/167 |
| 4,636,306 | 1/1987 | Radmall | 210/333.1 |
| 4,910,002 | 3/1990 | Grinstead | 423/243.08 |
| 4,921,610 | 5/1990 | Ford et al. | 210/321.69 |
| 4,980,066 | 12/1990 | Slegers | 210/321.69 |
| 5,047,154 | 9/1991 | Comstock et al. | 210/636 |
| 5,268,095 | 12/1993 | Barzuza | 210/143 |
| 5,273,665 | 12/1993 | White | 210/788 |

FOREIGN PATENT DOCUMENTS

| 55-20633 | 2/1980 | Japan | 423/243.08 |
| 61-234913 | 10/1986 | Japan | 423/243.08 |

Primary Examiner—Joseph W. Drodge
Attorney, Agent, or Firm—Sixbey, Friedman, Leedom & Ferguson

[57] ABSTRACT

A continuous filtration system for supplying an uninterrupted supply of filtrate from a solids-containing industrial process suitable for use by on-line automatic analyzers is provided. The continuous filtration system, which is particularly useful for filtering flue gas desulfurization process slurry to produce a solids-free filtrate for autoanalysis, includes a pair of filters connected in series which concurrently receive a tangential flow of slurry into the filter head that is discharged perpendicularly through a filtrate head. An automatic flushing system is provided to keep the filter membranes free of solid particles. An optional autoanalyzer for unfiltered slurry may also be included in the system.

18 Claims, 3 Drawing Sheets

TWO CONTINUOUS FILTRATION SYSTEM FOR SUPPLYING FILTRATE TO AUTOMATIC ANALYZERS

TECHNICAL FIELD

The present invention relates generally to systems for the continuous filtration of liquid streams containing solid particles to produce a solids-free filtrate and specifically to a continuous filtration system for the on-line filtration of flue gas desulfurization process slurry to produce a filtrate suitable for use by automatic flue gas desulfurization process analysis equipment.

BACKGROUND OF THE INVENTION

The analysis equipment used to measure and monitor key control process indicators and parameters of flue gas desulfurization processes and other industrial processes requires a dependable supply of filtered process liquor to insure the accurate and reliable analysis of the flue gas desulfurization or other industrial process. Analysis systems such as the automatic on-line flue gas desulfurization process control and monitoring system described in commonly owned co-pending U.S. patent application Ser. No. 08/302,438, filed Sep. 9, 1994, and entitled ON-LINE CONTROL AND MONITORING SYSTEM FOR WET LIME/LIMESTONE FLUE GAS DESULFURIZATION PROCESS, require an uninterrupted and consistent supply of filtered process slurry from the flue gas desulfurization process liquor to the automatic analyzers. Analysis systems used in conjunction with other industrial processes also require a solids-free filtrate so that an accurate analysis can be conducted. The samples required for automatic analysis in the laboratory are filtered without difficulty, and the analysis equipment is easily maintained and kept free from blockage by process solids. However, it has proven to be significantly more difficult to maintain on-line analysis equipment and to prevent plugging of analyzer fluid lines when process solids are continuously present. As a result, the accurate on-line analysis of process indicators and parameters while an industrial process is being simultaneously conducted has not been readily available.

Filter systems initially used to filter flue gas desulfurization process slurries to be analyzed in on-line analysis equipment experienced plugging of the filter membrane, resulting in low filtrate flows. The life expectancy of the filter membrane was also short due to high erosion by the slurry particles. In addition, corrosion of filter system components presented problems, and the replacement costs for the filter membranes was high. One filter design for a flue gas desulfurization process slurry filter concentrated slurry flow in a relatively small area of the filter membrane, which produced regions of low flow and low slurry velocity, referred to as dead zones, where solids settled. The slurry solids solidified on the filter membrane and rendered that particular membrane area inactive in the filtering process. As agitators were used to reduce these dead zones in the filter, the problems were compounded. The action of the agitators fractured the slurry solid crystals and generated ultra-fine particles that plugged the interstitial areas (pore spaces) of the filter membrane. This pluggage was tenacious and could only be removed by vigorous manual cleaning of the membrane. It was discovered that as the filtering area and thus the filtering capacity decreased, this filtering system could not deliver the minimum filtrate flow requirements to the flue gas desulfurization process analyzers. At such low filtrate flows, manual disassembly of the filter housing, manual cleaning of the filter medium and manual reassembly of the housing is required to remove the deposited slurry solids and restore the filtering capacity of the filter membrane.

One filtration system initially proposed for providing flue gas desulfurization process slurry filtrate to an automatic analyzer system, which used custom made filter membranes, experienced extremely short membrane life because the slurry inlet was configured to direct the slurry flow into the filter perpendicular to the filter membrane. As a result, a steady stream of abrasive flue gas desulfurization process slurry was focused directly at the face of the membrane in a concentrated area. This caused failure of the filter membrane because a large hole was quickly worn in the membrane. Consequently, the filter membranes of this system had a very short useful life and were costly to replace.

The prior art has proposed other filtration systems for solid-liquid separation. For example, a filter system for industrial process plant effluents which produces a filtrate suitable for on-stream analysis from a solids-containing effluent stream is disclosed in a publication by Collins Products Company of Livingston, Tex. describing their Models 9000 and 8500 filter systems. These systems are designed to provide a continuous supply of effluent filtrate to process analyzers and include a bypass flow to clean the filter element. However, the solids-containing effluent stream is directed into the filter along a path perpendicular to the filter membrane, and agitators are used to clean the filter membrane. Both of these features have been demonstrated to decrease dramatically the useful life of the filter membrane when a flue gas desulfurization process slurry is filtered.

In U.S. Pat. No. 3,598,238 to Collins a filter apparatus is disclosed wherein the fluid to be filtered for analysis enters the apparatus at an orientation that is not perpendicular to either of two filter membranes. A valve system blocks flow through one of the membranes so this membrane can be cleaned by the swirling action of the fluid in the filter body entering the other fluid membrane. This swirling action will provide some cleaning of the filter membrane; however, fines or solid particles embedded in the membrane or screen cannot be easily removed in this system so that eventually the effective filter area and capacity will be reduced unless the filter screen is removed and cleaned manually. In addition, only one filter membrane is available for use while the other is being cleaned.

U.S. Pat. No. 4,636,306 to Radmall also discloses parallel filters with automatic backwashing capability, wherein fluid flows through only one filter unit at a time so that the second unit can be cleaned. The fluid flow through these filter units is essentially perpendicular to the filter unit so that the membrane is likely to wear out quickly. Additionally, in this system, as one filter unit is being washed, only one filter unit is available at any one time. This reduces the capability of the filtration system by limiting the available surface area of the system to that of one filter unit.

U.S. Pat. No. 4,178,248 to Porter et al. discloses a cartridge type of filter which includes a tangential bypass flow perpendicularly across the filter membrane from the outlet to the inlet direction to provide a sweeping removal flow that clears the inlet side of clogging material. This type of arrangement may be satisfactory for pleated cartridge type filters shown, but is of limited utility in providing a continuous supply of filtered flue gas desulfurization process or other industrial process liquor to automatic analysis equipment. U.S. Pat. No. 5,273,665 to White also discloses a cartridge-type filter. The fluid flow is directed tangential to the filter medium by the conical configuration of the chamber, and solids are removed by swirl separation.

U.S. Pat. No. 5,268,095 to Barzuza discloses a self-cleaning filter unit. However, the fluid flow inlet is perpendicular to the filter medium, and a rotating nozzle directs the fluid against the filter medium.

U.S. Pat. No. 3,421,835 to McCarty is of interest for its disclosure of a pair of filters with a backwash capability useful for solid-liquid separation in a dry cleaning mechanism.

The prior art, therefore, has failed to suggest a simple, reliable continuous filtration system for providing an uninterrupted supply of flue gas desulfurization process slurry or other industrial process filtrate for automatic on-line analysis with a self-cleaning, nonplugging filter membrane and a simple, non-corroding filter housing that may be easily automatically operated and maintained.

SUMMARY OF THE INVENTION

It is a primary object of the present invention, therefore, to overcome the disadvantages of the prior art and to provide a simple, reliable continuous filtration system capable of supplying an uninterrupted supply of filtrate from a solids-containing industrial process slurry to an on-line automatic analysis system.

It is another object of the present invention to provide a continuous filtration system for flue gas desulfurization process slurry which provides a continuous supply of slurry filtrate to an on-line automatic analysis system.

It is a further object of the present invention to provide a continuous filtration system for a solids-containing industrial process slurry which provides maximum filtrate flow to an automatic analysis system and automatically backflushes the filter membrane with minimal impact on filtrate flow.

It is yet another object of the present invention to provide a continuous filtration system for producing filtrate for automatic analysis from a solids-containing industrial process slurry which returns unused slurry to the process.

It is yet a further object of the present invention to provide a continuous filtration system for a solids-containing industrial process slurry which maximizes the useful life of the filter membrane.

It is still another object of the present invention to provide a continuous filtration system for a solids-containing industrial process slurry which minimizes corrosion of the system components.

It is a still further object of the present invention to provide a continuous filtration system for a solids-containing industrial process slurry which concurrently provides a solids-free filtrate fraction for automatic on-line analysis and a solids-containing fraction for automatic analysis.

The aforesaid objects are achieved by providing a continuous filtration system for receiving a supply of industrial process slurry, such as flue gas desulfurization process slurry from a wet lime/limestone flue gas desulfurization process. The continuous filtration system continuously filters the slurry to provide an uninterrupted supply of slurry filtrate to an automatic on-line analysis system for analyzing the slurry filtrate to monitor key process indicators. The continuous filtration system includes a source of process slurry, a source of service water, a pair of filters fluidically connected in series to the slurry and water supplies, a slurry return fluidically connected to the industrial process, and a filtrate supply outlet fluidically connecting the pair of filters with an automated analysis system to supply filtrate to the analysis system. Each of the pair of filters includes a housing with a slurry inlet and a filtrate outlet with a filter membrane supported between the slurry inlet and the filtrate outlet. A control signal activates a timed automatic flushing system to isolate the filters so that a backflush and foreflush of water through the filter membrane and housing occurs. A timed purge cycle purges water from the filtration system so it is ready to produce additional slurry filtrate for analysis. The continuous filtration system also includes an analysis system for automatically analyzing unfiltered slurry from the source of process slurry.

Other objects and advantages will be apparent from the following description, claims and drawings.

DESCRIPTION OF THE PREFERRED EMBODIMENTS

Figure 1:
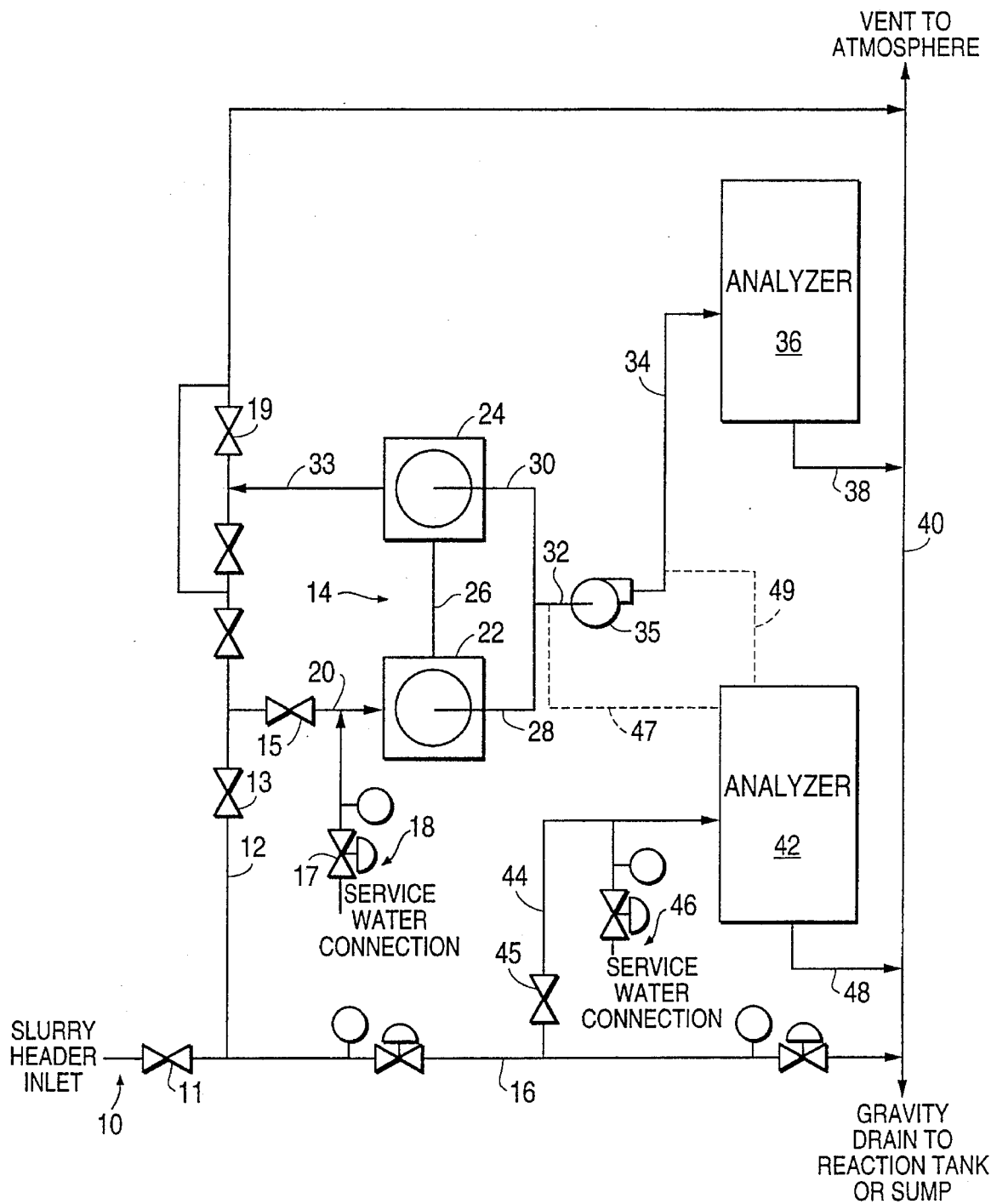
FIG. 1 is a flow chart which illustrates the continuous filtration system of the present invention in an on-line chemical monitoring system for a flue gas desulfurization process.

Automatic analysis and monitoring systems require a continuous supply of filtered, solids-free liquid for the performance of accurate chemical analyses. Flue gas desulfurization and many other industrial process slurries typically contain sufficient solids to quickly clog and thus disable the analysis equipment used to monitor key process indicators. The present invention provides a filtering system which supplies an uninterrupted and consistent supply of filtered process liquor to automatic analysis equipment. This filtering system will be described for use with a flue gas desulfurization process. However, it can be used equally advantageously with other industrial processes that produce solids-containing process liquor which can be analyzed to determine key process indicators or parameters.

The continuous filtration system of the present invention is an improvement of a filtering system initially developed from available filter components to continuously filter flue gas desulfurization process slurry. The membranes of the commercially available filters quickly became clogged, which reduced filtrate flow to the analyzers, and the filter membranes had a short life expectancy because the filter design quickly eroded the membranes. The cost of membrane replacement was unacceptably high because of the nonstandard size membrane used by these filters. An additional problem was presented by the corrosion of the filter internal components. The continuous filtration system of the present invention is a highly reliable and cost effective system which does not present these problems.

The continuous filtration system of the present invention operates generally as follows: Flue gas desulfurization process slurry concurrently enters a pair of filters in housings in a series configuration through slurry inlets positioned tangentially to filter membranes. The pressure of the incoming slurry forces it through the filter membranes, and the filtrate accumulates in collection channels and vanes formed in the filter housing. Fluid pressure forces the filtered liquor through a discharge outlet in each filter, and the two filtrate streams are combined and directed to the on-line analyzers for the analysis of desired process indicators. Eventually fine slurry particles will become embedded in the interstices (pore spaces) of the filter medium, which decreases filtering efficiency and reduces the flow of slurry filtrate to the analyzers. The present invention includes an automatic filter flushing system which flushes and purges the fines from the membrane pores onto the supply side of the membrane so that these solids can leave the filter. The automatic flushing system may be actuated by appropriate signals from a control mechanism associated with the automatic analysis system after a predetermined number of analyses have been performed.

The present continuous filtration system meets or exceeds the following minimum performance criteria, which ensure accurate and reliable operation of on-line automatic analysis equipment used to analyze process liquor:

1. Continuous flow rate of filtrate to analyzers of 100 to 150 ml/min.
2. Inlet slurry flow rate of 4 to 8 gpm.
3. Inlet slurry pressure of 15 psi.
4. Filter housing capable of withstanding pressures of 50 psi.

In addition, the present filtration system satisfies the following objectives:

1. Maximizes the on-line ability of the filtering process without plugging the filter components.
2. Maximizes filter membrane longevity.
3. Maximizes self-rinsing characteristics of the filter membrane.
4. Minimizes moving parts within the filter housing.
5. Minimizes corrosion of the filter membrane and housing.
6. Minimizes overall cost of the filter membrane, housing and controls.
7. Provides a completely automatic filter flushing system.
8. Maximizes ease of maintenance and replacement of filter medium.
9. Uses standard sizes of commercially available filter media.

Referring to the drawings, FIG. 1 is a schematic flow diagram of the continuous filtration system of the present invention in combination with an automatic on-line flue gas desulfurization process analysis system.

Slurry from a wet flue gas desulfurization system (not shown), such as the wet lime/limestone flue gas desulfurization system described in commonly owned U.S. Pat. No. 5,034,204, the disclosure of which is hereby incorporated herein by reference, is directed into a process slurry header inlet 10. Because the slurry must be filtered so that it can be reliably analyzed by different kinds of automatic on-line analyzers, it is then directed along a fluid line 12 to the continuous filtration system 14 of the present invention. A slurry bypass line 16 is also connected to the slurry header inlet so that the slurry can be routed around the continuous filtration and on-line analysis systems and returned to the flue gas desulfurization system reaction tank (not shown) if necessary or desired. A service water connection 18 is connected to a fluid line 20 which supplies slurry to the continuous filtration system 14. This service water connection ensures a ready supply of water for flushing the filter heads of the filtration system 14.

The continuous filtration system 14, which will be described in greater detail below in connection with FIG. 2, includes a pair of filters 22 and 24 connected in series by a conduit 26. Filtrate discharge lines 28 and 30 are provided for each filter 22 and 24, respectively. The filtrate discharge lines combine to form a single slurry filtrate outlet 32. A fluid return line 33 directs excess slurry from the filtration system 14 back to the flue gas desulfurization system.

From the slurry filtrate outlet 32, the filtrate can be pumped by a pump 35, or will flow at a rate based on the inlet slurry pressure to the filter inlet fluid line 20, along a conduit 34 to one or more automatic analyzers for performing desired analyses of the slurry filtrate to obtain information about key flue gas desulfurization process indicators. The analyses performed on the flue gas desulfurization process slurry filtrate by the automatic analyzers may be those described in commonly owned co-pending U.S. patent application Ser. No. 08/302,438, filed Sep. 9, 1994, and entitled ON-LINE CONTROL AND MONITORING SYSTEM FOR WET LIME/LIMESTONE FLUE GAS DESULFURIZATION PROCESS, the disclosure of which is hereby incorporated herein by reference. Only one analyzer 36 that conducts analyses on slurry filtrate is shown in FIG. 1; however, any number of analyzers may be used in connection with the continuous filtration system described herein. The analyzer 36 is connected through line 38 to a drain and vent line 40 which directs the filtrate after it has been analyzed, by gravity back to the flue gas desulfurization system reaction tank (not shown) or to a sump (not shown). Line 40 also provides a vent to atmosphere for the system.

In addition to the automatic analyzer 36, which requires a continuous supply of slurry filtrate to function properly, FIG. 1 also shows an analyzer 42 which receives unfiltered slurry from the flue gas desulfurization system through a slurry supply line 44 connected through line 16 to the slurry inlet 10. After the analysis has been conducted, the slurry is directed to the drain line 40 through a slurry drain line 48. A service water connection 46 supplies water for the analysis and to flush the analyzer. The kinds of analyses performed on the unfiltered flue gas desulfurization slurry by analyzer 42 include, for example, a total carbonate analysis. Through this measurement, this type of analyzer could also be used to monitor limestone utilization by the flue gas desulfurization process or measure limestone loading going into the scrubber (not shown). High carbonate content could be used as an indicator of operating problems such as limestone blinding. Similarly, carbonate content could be used with this invention to control limestone addition to the flue gas desulfurization process.

The analyzer 42 could be eliminated, if desired, or replaced by another analyzer that performs analysis on slurry filtrate rather than unfiltered slurry. An additional filtrate supply line 47 from the slurry filtrate outlet 32 or a line 49 from the discharge line 34 of the slurry filtrate outlet pump 35 would be required for this application.

A number of valves are positioned at locations in the filtration system which permit maximum control over the fluid flow and maintenance of the desired fluid pressure within the system. For example, valves 13 and 15 regulate slurry flow to the filter system 14, and valve 17 regulates both the flow and pressure of water to the filter system 14.

The slurry delivery system may be isolated from the rest of the slurry monitoring system for cleaning by the automatic backwashing system by closing valves 13 and 19. The flow of slurry to the analyzer 42 may be controlled by valve 45. Slurry flow to the entire filtration system may be regulated by valve 11. These valves are preferably automatically controlled by air actuation, solenoid actuation or actuation by any other suitable means in response to a control system (not shown) which monitors the analysis and filtration system.

Figure 2:
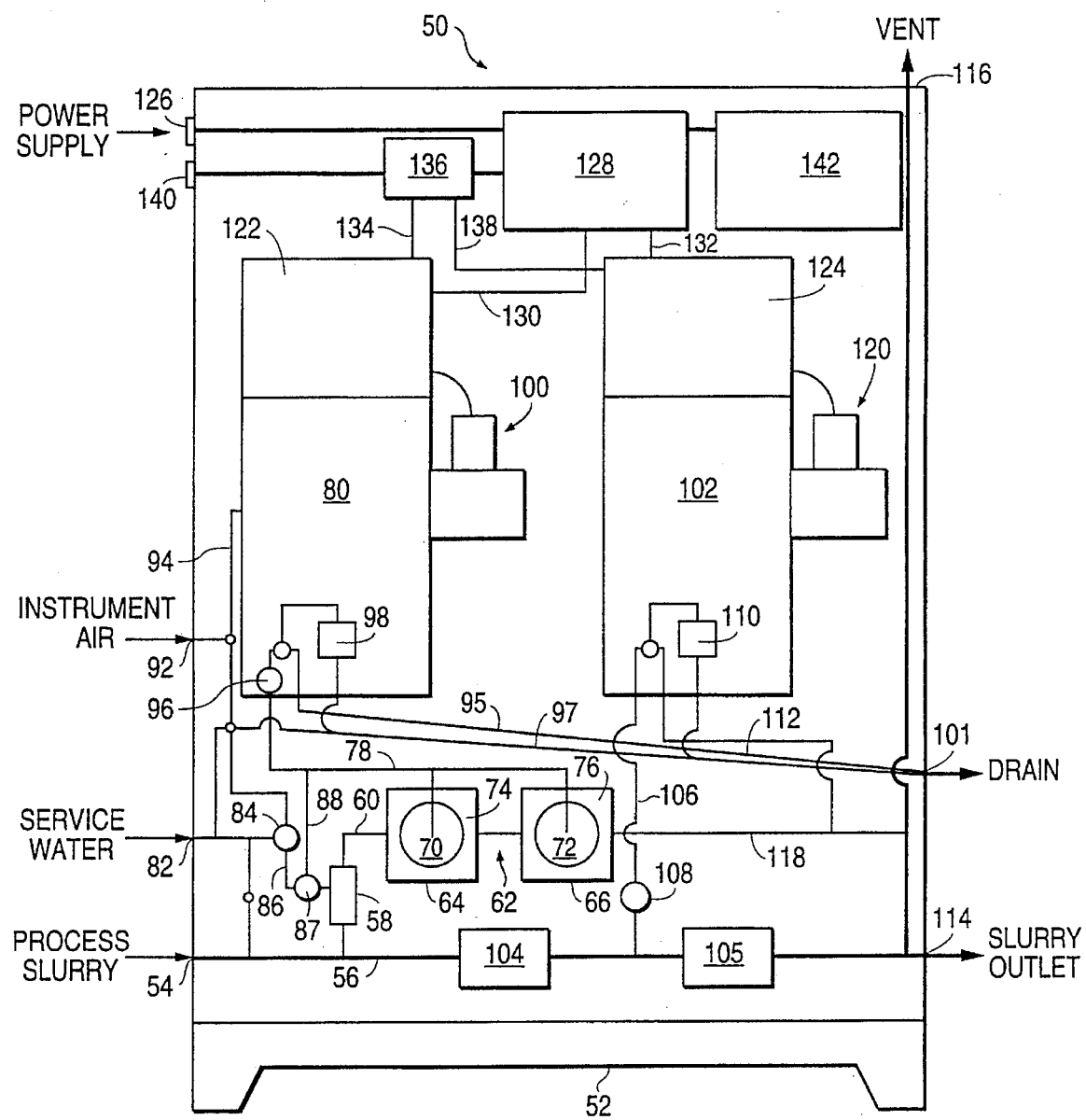
FIG. 2 illustrates schematically one embodiment of the continuous filtration system of the present invention with on-line automatic analyzers for concurrently analyzing a slurry filtrate fraction and an unfiltered slurry fraction of a flue gas desulfurization process.

FIG. 2 illustrates one embodiment of an on-line flue gas desulfurization process chemistry monitor which employs the continuous filtration system of the present invention. This embodiment is purely exemplary, and other on-line chemistry monitor arrangements could be used with the present filtration system. The on-line chemistry monitoring system 50 shown in FIG. 2 is mounted and contained within a supporting housing 52. The housing preferably contains doors (not shown) for easy access which can be sealed to protect the filtration system and analyzers from a hostile environment. A drain (not shown) is preferably located in the bottom of the housing so that any leaked or overflow slurry or filtrate does not stay in the housing. Slurry from a flue gas desulfurization process enters the monitoring system 50 through a process slurry inlet 54. The slurry is directed from the inlet 54 into a slurry line 56 and from slurry line 56 through a valve 58 into a filter slurry inlet 60 and into the filtration system 62. Flow control valve 104 regulates the slurry flow and pressure through the main slurry line 56 to allow an adequate supply of slurry to pass through valve 58 to the slurry filter inlet 60.

The filtration system 62 includes a pair of filters 64 and 66 which are connected in series. Each of the filters 64 and 66, respectively, includes filter membranes 70 and 72 supported in housings 74 and 76. Slurry is directed into the filter 64 from the slurry filter inlet 60 along a path that is tangential to the surface of the filter membrane 70, as will be explained in detail below. Likewise, slurry is directed into the filter 66 along a path that is tangential to the filter membrane 72. Filtrate from the filters 64 and 66 is discharged from each filter into a single filtrate outlet line 78, which is connected to an analyzer 80. A water inlet 82 provides service water for flushing the filter membranes 70 and 72 to clean them. Water is directed through a valve 84 into a bypass line 86. Water for backflushing the filter membranes 70 and 72 flows through the bypass line 86, through a valve 87 and another bypass line 88 into the slurry filtrate line 78 and then into each filter 64 and 66 from the filtrate outlet side, as will be described below. Additionally, water can also flow through valve 87 through slurry filter inlet line 60, through the inlet side of the filters, and out slurry filtrate line 78 and drain 95.

An air inlet 92 provides air to actuate the valves as required for the switching to automatic filter flushing operation and to vent the analyzers and their instrumentation. An air line 94 directs air to the analyzer electronics.

Entry of the filtrate into the analyzer 80 is controlled by a valve 96. The filtrate is directed to an analysis cell 98 in the analyzer 80 where the analysis is actually conducted. Reagents and solutions required for the analysis, such as standards and titrants, are held in a reagent storage module 100 and are automatically metered or pumped to the analysis cell 98 as needed. After the analysis has been conducted, the filtrate is directed from the cell 98 through a drain line 97 to a drain 101. Excess filtrate in the analyzer 80 flows to the drain 101 along a drain line 95. The drain line 97 is also used to conduct service water to the drain 101. Bypass line 88 is used to direct service water to analysis cell 98 to wash the cell between each analysis. This wash water flows through valve 96 and drains through line 97 and drain 101. Drain 101 is a gravity drain, which requires drain lines 95 and 97 to be positioned within the system to provide a downward grade to the drain.

As discussed in connection with FIG. 1, it is often desired to analyze unfiltered slurry while a flue gas desulfurization process is being conducted. Other on-line analyses of flue gas desulfurization slurry can be conducted by an analyzer 102. The slurry is directed through the slurry line 56 to a flow control valve 104 and through a slurry supply line 106 to the analyzer 102. A pressure gauge 108 is provided to monitor slurry flow, which is regulated by flow control valve 105 on the basis of the pressure of the slurry. The slurry analysis is conducted in an analysis cell 110 in the analyzer 102. After analysis, the slurry is directed into drain line 97 to the drain 101. Excess slurry is discharged from the analyzer 102 through a slurry discharge line 112. The excess slurry is then directed through the fluid return line 118 through vent pipe 116 to exit the system at a slurry outlet 114. Excess slurry may be returned to the flue gas desulfurization process reaction tank (not shown). A vent to atmosphere is provided in vent pipe 116 to vent the system and allow gravity drains to operate properly at atmospheric pressure.

The analyzer 102 also includes a reagent storage module 120 for holding and automatically dispensing the reagents, standards and other solutions required for the analysis process.

Each of the analyzers 80 and 102 includes respective sections 122 and 124 which house the electronics and electrical connections required to run the analyzers and the continuous filtration system, including the autoflush or automatic backflush for cleaning the filter membranes. A power supply 126, which preferably provides a source of 110 volts of alternating current, is connected to a circuit box 128, which provides electrical power to the analyzers 80 and 102 through electrical connections 130 and 132, respectively. Air from the air inlet 92 is directed to sections 122 and 124 of the analyzers through air line 94 to keep the electronics vented and cool and for purging any offgases. As filtrate is analyzed in the analyzer 80, signals are generated by the analyzer and sent by a signal line 134 to a data link 136. Signals from the analysis of slurry by analyzer 102 are sent by a signal line 138 to the data link 136. The data link is connected to a data acquisition system input/output link 140. The data generated by the analysis can be handled in different ways as discussed in detail in copending U.S. patent application Ser. No. 08/302,438, filed Sep. 9, 1994, entitled ON-LINE CONTROL AND MONITORING SYSTEM FOR WET LIME/LIMESTONE FLUE GAS DESULFURIZATION PROCESS.

FIG. 2 also illustrates the automatic filter flushing and cleaning system of the present invention. An autoflush control 142 is provided to receive signals from the analyzers 80 and 102 and to actuate the automatic flushing system. Signals from each analyzer 80 and 102 are received by the autoflush control 142 and are counted to determine the number of analyses performed. After a predetermined number of analyses have been performed by each analyzer, the flushing mechanism is actuated. The valves 58 and 96 are air actuated to isolate the filter system 62. Air actuated valves 84 and 87 are opened so that water can be directed into the filter system 62 through the flush water inlet 82 to enter each filter 64 and 66. The flush water flows under pressure through each filter membrane 70 and 72 from line 78 on the outlet side to the inlet side, effectively blackflushing each membrane and flushing the filter housings 74 and 76. The flushing mechanism is actuated to run for a predetermined length of time, the length of which will vary depending on such factors as the number of analyses to be conducted and the size of the solid particles in the slurry. After the prescribed flushing time, valves 87, 58 and 96 are actuated to allow the service water to flow into the slurry filter inlet 60 and out through line 78 to drain 95 and drain 101. A timed purge cycle is also preferably included to allow a sample of diluted slurry to purge any water before the next analysis measurement. Alternatively, a programmable logic controller (PLC) can be used for complete control of the flush cycle and for initiation of the automatic analysis.

Filtering efficiency is decreased over time as fine particles of slurry become embedded in and clog the pores of the filter medium. As the production rate of filtrate is decreased by the clogged filter medium, the flow of filtrate to the analyzers is likely to fall below the minimum flow rate acceptable to automatic analysis equipment. The continuous filtration system has been designed to keep filtrate flow rates above these minimum acceptable flow rates. Flushing the filter membranes 70 and 72 pushes fines out of the membrane pores and back onto the supply side of the filter membranes where these solids can exit through bypass line 118 through slurry outlet 114 and drain 101, respectively. Unlike the tangential slurry inlet flow, the backflush flow is perpendicular to the filter membrane, which is a more effective orientation for cleaning the membrane. This automatic backflushing system keeps the filter membranes in a clean condition and minimizes manual removal and cleaning of the filters and membranes. Filtration capacity is maximized by the flushing system by monitoring analyzer status and performing sequential flush/backflush operations during periods when the analyzers do not require slurry filtration. The plumbing connections of the slurry feed and the backflush system have been optimized to provide maximum filtrate flow to the analyzers and to perform the backflush operation with minimal impact on filtrate supply to the analyzers. It has been determined that acceptable filter reliability and performance can be maintained by flushing the filter every 2 to 4 hours. Other intervals may also be effective, however.

FIGS. 3a, 3b, 4a and 4b illustrate details of the filter heads used on the filter housings 74 and 76 in the continuous filtration system of the present invention. The flue gas desulfurization slurry enters the housings of filters 64 and 66 (FIG. 2) in a series configuration, flowing concurrently to each housing. The filtrate streams leaving the filters are then combined and sent to the analyzers. Unlike prior filter designs, the filter of the present invention does not concentrate slurry flow to a relatively small area of the filter membrane and does not agitate the slurry on the inlet side of the membrane. Concentrating the slurry on a relatively small area of the filter membrane produced regions of low flow and low slurry velocity or dead zones where slurry solids settled and rendered the membrane incapable of properly filtering the slurry. The agitators used by prior art filters to reduce dead zones only compounded the problem by fracturing the flue gas desulfurization slurry crystals and generating ultrafine particles which plugged the interstitial areas of the filter membrane. Vigorous manual cleaning was then required to remove this tenacious pluggage, which prevented the filters from delivering the minimum filtrate flows required for on-line analyzers.

The filter design of the present invention does not employ agitators or any other moving parts within the filter housing and utilizes a tangential slurry inlet or delivery port which maximizes the effective filtering area of the membrane. A central perpendicular filtrate discharge port in combination with the tangential slurry inlet causes incoming solids particles constantly to pick up a portion of the solids particles that have accumulated on the membrane and carry these solids to the slurry discharge. A perpendicular slurry inlet configuration initially used for the system focused a steady stream of abrasive slurry particles directly at the filter membrane, which quickly wore a hole in the membrane and caused it to fail. Abrasive wear of the filter membrane surface is virtually eliminated by the tangential slurry inlet port design shown in FIGS. 3a and 3b.

Figure 3B:
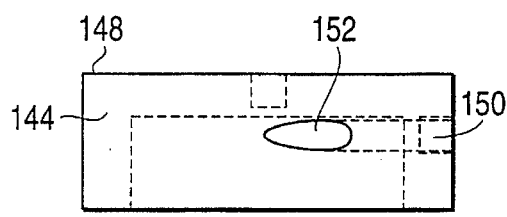
FIGS. 3a and 3b illustrate, respectively, a front and a cross-sectional view along line 3a—3a of a filter slurry head for the continuous filtration system of the present invention.
Figure 3A:
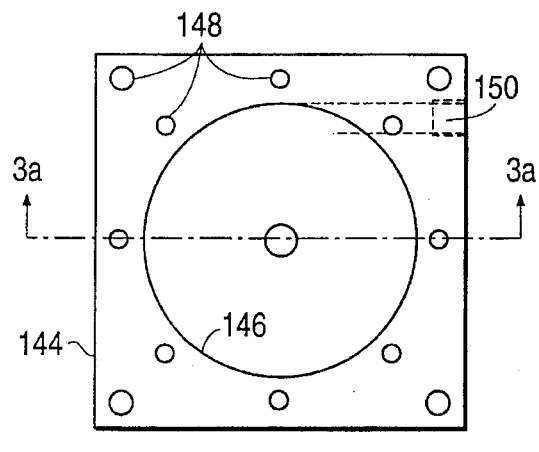

FIG. 3a illustrates, in top view, the slurry head 144 of a filter, such as filters 64, 66, of the continuous filtration system of the present invention. The slurry head may have a substantially rectangular or square configuration as shown which supports a substantially circular filter membrane (not shown) that would be visible through the circular opening 146 in the filter head. A plurality of holes 148 is provided to secure the filter head to the filter housing (not shown). A slurry inlet 150 is positioned in the slurry head to direct slurry along a path tangential to the circumference of the filter membrane. FIG. 3b is a cross-sectional view of the slurry head 144 taken along line 3a—3a in the direction of the arrows. The orientation of the slurry inlet discharge port 152 which directs the slurry flow tangential to the filter medium is shown in FIG. 3b. This tangential slurry flow, in addition to minimizing abrasion of the membrane, also provides a self-cleaning action to the filter surface. An optimum slurry inlet pressure of 15 psi has been demonstrated to provide a consistent filtrate flow.

Unlike the filters previously used to filter flue gas desulfurization slurry, which required costly custom sized filters, the filter housing of the present invention accepts a commercially available 142 mm Teflon filter membrane with a preferred pore size of 0.45 micron, although other pore sizes could also be used. A porous backing material (not shown) is provided on the clear liquor side of the membrane to help support the membrane. The pressure of the incoming slurry provides the driving force for liquor to flow through the pores of the filter membrane to separate the solids from the process liquor. A membrane with a pore size of 0.45 micron is a very efficient medium for filtering solids from flue gas desulfurization slurry while minimizing pluggage of the interstitial areas (pore spaces) with collected solids. A majority of the filtered solids are then removed from the face of the filter medium by the swirling tangential flow of the incoming slurry.

Figure 4B:
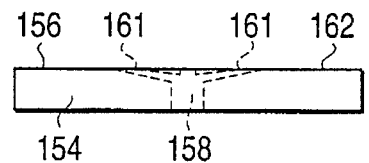
FIGS. 4a and 4b illustrate, respectively, a front and a cross-sectional view along line 4a—4a of a filtrate head for the continuous filtration system of the present invention.
Figure 4A:
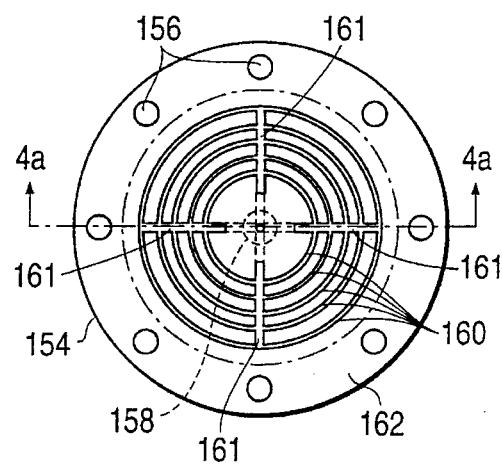

FIGS. 4a and 4b illustrate, respectively, in top and cross-sectional views, the filtrate head 154 of the present filter system. The filtrate head 154 preferably has a substantially circular configuration and includes a plurality of holes 156 which are used to secure the head to the filter housing (not shown). The filtered slurry filtrate on the clean side of the filter medium or membrane (not shown) flows into a plurality of concentric collection channels 160, which connect to collection vanes 161, which connect to the filtrate discharge port 158 where the filtrate accumulates. The collection channels 160 have been demonstrated to speed up the filtration rate and facilitate transport of the filtrate to the collection discharge port 158.

The slurry and filtrate head designs simplify access to the filter membrane for easy removal and replacement. In addition, a standard membrane size is employed in the filters of the present invention, which allows the use of a wide variety of mesh sizes and lower cost material options. Moreover, the heads 144 and 154 are formed of nonmetallic, corrosion-resistant materials to maximize cost and increase the life expectancy of the filtration system. The filter slurry head 144 is preferably formed of polypropylene, and the filtrate head 154 is preferably formed of acrylic plastic.

The continuous filtration system of the present invention has been demonstrated to be very reliable in providing filtered flue gas desulfurization process liquor which meets the exacting needs of automatic analyzers. Filters of the design shown and described herein have operated for over a month without requiting changing of the filter membranes. The automatic backflushing mechanism, moreover, has permitted the system to maintain a continuous filtrate or effluent liquor flow rate of over 100 milliliters/minute.

The continuous filtration system of the present invention has been described primarily with respect to its use in providing filtrate for analysis in connection with a flue gas desulfurization process. However, it is contemplated that the continuous filtration system described herein could be used to provide a continuous, uninterrupted flow of filtrate from a solids-containing slurry or the like from any industrial process to on-line automatic analyzers or other sensitive equipment.

Industrial Applicability

The continuous filtration system of the present invention will find its primary applicability in producing a continuous supply of filtered slurry from a flue gas desulfurization process to on-line automatic analyzers for analyzing key flue gas desulfurization process indicators. The present filtration system will also be useful in providing a supply of filtrate from a solids-containing fluid for processing by automatic analyzers or any other equipment that requires an uninterrupted, reliable supply of solids-free liquid.

We claim:

1. A continuous filtration system for producing an uninterrupted supply of a solids-free filtrate from a solids-containing industrial process slurry for the automatic on-line analysis of components of the filtrate by an automatic analyzer system, wherein said continuous filtration system comprises:

(a) a supply of a solids-containing slurry to be filtered;
   (b) a pair of filter elements fluidically connected together in series and selectively fluidically connected and disconnected to the supply of slurry and fluidically connected to a source of water;
   (c) a filtrate outlet connected to the filter elements and selectively fluidically connected and disconnected to an automatic analyzer system for analysis of said filtrate;
   (d) a control system controllable to automatically and selectively disconnect the filter elements from the slurry supply and the automatic analyzer system and to direct water from the water source through said filter elements from the filtrate outlet toward the slurry supply and then from the water source through the filter elements toward the filtrate outlet in response to a predetermined signal corresponding to the performance of a predetermined number of analyses performed in the analyzer system and then to automatically m-connect the filter elements to the slurry supply and the filtrate outer to the analyzer system; and
   (e) a drain fluidically connected to the automatic analyzer system and the water source to direct excess fluids away from the filter elements and the analyzer system.

2. The continuous filtration system described in claim 1, wherein each of said pair of filter elements includes:

(a) a housing supporting a slurry head spaced toward the slurry supply from a filtrate head;
   (b) a planar filter membrane positioned between the slurry head and the filtrate head;
   (c) a slurry inlet in the slurry head oriented to direct a flow of slurry into the filter element tangential to the filter membrane; and
   (d) a filter outlet in the filtrate head oriented to direct a flow of filtrate out of the filter element perpendicular to the filter membrane and into a plurality of filtrate collection channels.

3. The continuous filtration system described in claim 2, wherein said control system includes:

(a) an autoflush control system electronically connected to a circuit box connected to said automatic analyzer system, said autoflush control system being connected to said slurry supply and to said water source;
   (b) a plurality of valves located in the fluid connections between said slurry supply, said water source, said filtrate outlet and said analyzer system, wherein said valves are actuatable by said autoflush control system to selectively direct fluid flow in response to said predetermined signal after said predetermined number of analyses have been performed; and
   (c) a data acquisition system input/output link electronically connected to said autoflush control system.

4. The continuous filtration system described in claim 3, wherein said system further includes an automatic flushing system to remove solid particles from said filter membranes, said automatic flushing system comprising an autoflush controller electronically connected to said autoflush control system, to said data acquisition system input/output link and to said plurality of valves, said source of water, and said filtrate outlet, wherein said autoflush controller receives said predetermined signal and actuates said valves to prevent slurry flow through said filter elements and to cause water from said source of water to flow into said filter elements through said filtrate outlet and out said slurry inlets and then through said slurry inlets and out said filtrate outlet to said drain.

5. The continuous filtration system described in claim 4, further including an automatic analysis system fluidically connected directly to said slurry supply and fluidically connected to a slurry outlet.

6. The continuous filtration system described in claim 2, wherein said slurry heads have a substantially rectangular configuration and are formed of polypropylene.

7. The continuous filtration system described in claim 2, wherein said filtrate heads have a substantially circular configuration and are formed of an acrylic plastic.

8. The continuous filtration system described in claim 7, wherein said filtrate heads include a plurality of concentric channels and collection vanes integrally formed in said filtrate heads and spaced outwardly from respective filter outlets.

9. The continuous filtration system described in claim 1, wherein said industrial process is a wet lime or limestone slurry flue gas desulfurization process.

10. A continuous filtration system for producing an uninterrupted supply of a solids-free filtrate from a wet lime or limestone slurry flue gas desulfurization process slurry for the on-line automatic analysis of selected process indicators of tho flue gas desulfurization process, said continuous filtration system comprising:

(a) a source of flue gas desulfurization process slurry to be analyzed;
   (b) a pair of filter elements fluidically connected together in series and fluidically connected to the source of slurry wherein each of said filter elements includes:

(i) a housing supporting a slurry head spaced toward the slurry source from a filtrate head;

(ii) a planar filter membrane positioned between the slurry head and the filtrate head;

(iii) a slurry inlet head oriented to direct a flow of slurry into the filter element tangential to the filter membrane; and (iv) a filtrate outlet in the filtrate head oriented to direct a flow of filtrate out of the filter element perpendicular to the filter membrane fluidically connected to an automatic analyzer system;

(c) a source of water fluidically connected to the filter elements;

(d) a control system controllable to automatically and selectively fluidically isolate the falter elements from the slurry source, the water source and the automatic analyzer system and to direct water from the water source through said filter elements from the filtrate outlets to the slurry source and then from the water source through the filter elements toward the filtrate outlets in response to a predetermined signal corresponding to a selected number of analyses having been performed by the automatic analyzer system; and (e) a drain fluidically connected to the automatic analyzer system and the water source to direct excess fluids away from the filter elements and the automatic analyzer system.

11. The continuous filtration system described in claim 10, wherein said control system includes:

(a) an autoflush control system electronically connected to said automatic analyzer system, to said slurry source and to said water source;

(b) a plurality of valves located in the fluid connections between said slurry source, said water source, said filtrate outlets and said analyzer system, wherein said valves are actuatable by said autoflush control system to selectively direct fluid flow in response to said predetermined signal; and (c) a data acquisition system input/output link electronically connected to said autoflush control system.

12. The continuous filtration system described in claim 11, wherein said system further includes an automatic flushing system to remove solid particles from said filter membranes, said automatic flushing system comprising:

(a) an autoflush controller electronically connected to said autoflush control system, to said data acquisition system input/output link and to said plurality of valves;

(b) said source of water; and (c) said filtrate outlets, wherein said autoflush controller receives said predetermined signal and actuates said valves to prevent slurry flow through said filter elements and to cause water from said source of water to flow into said filter elements through said filtrate outlets and out said slurry inlets and through said slurry inlets and out said filtrate outlets to said drain.

13. The continuous filtration system described in claim 12, further including an automatic analysis system fluidically connected directly to said slurry source and fluidically connected to a slurry outlet.

14. The continuous filtration system described in claim 10, wherein said slurry heads have a substantially rectangular configuration and are formed of polypropylene.

15. The continuous filtration system described in claim 10, wherein said filtrate heads have a substantially circular configuration and are formed of an acrylic plastic.

16. The continuous filtration system described in claim 15, wherein said filtrate heads include a plurality of concentric channels and collection vanes integrally formed in said filtrate heads and spaced outwardly from respective filtrate outlets.

17. A method for automatically producing a supply of slurry filtrate from a wet lime or limestone slurry flue gas desulfurization process for the analysis of selected flue gas desulfurization process indicators including the steps of:

(a) concurrently directing a flow of flue gas desulfurization process slurry tangentially through a pair of filter membranes connected in series to produce a slurry filtrate;

(b) directing the slurry filtrate to at least one automatic analyzer, analyzing the filtrate as required and obtaining signals corresponding to numbers of analyses performed, and transmitting said signals to an autoflush control system;

(c) when a predetermined number of signals corresponding to a selected number of analyses performed on the slurry filtrate have been transmitted to said autoflush control system, selectively actuating a plurality of valves to prevent slurry flow through said filter membranes and to cause service water to flow perpendicularly through said membranes in a direction opposite the slurry flow during step (a);

(d) permitting the service water to flow through said membranes for a predetermined time and then deactuating said valves to cause slurry flow through said filter membranes to produce slurry filtrate for analysis by said at least one automatic analyzer; and (e) repeating steps (a) through (d) as necessary to obtain required information from the analysis.

18. The method described in claim 17, wherein said method further includes the steps of concurrently directing a flow of unfiltered flue gas desulfurization process slurry to an automatic analyzer, conducting a selected analysis on said unfiltered slurry, transmitting signals corresponding to the data obtained to an autoflush control system, and directing the used unfiltered slurry to a slurry outlet.

\* \* \* \* \*